United States Patent [19]

Skwarek et al.

[11] Patent Number: 5,531,703
[45] Date of Patent: Jul. 2, 1996

[54] APPLICATOR FOR SEMISOLID MEDICATIONS

[75] Inventors: Gary M. Skwarek, Memphis; Stephen J. Morfit, Germantown, both of Tenn.

[73] Assignee: Schering-Plough HealthCare Products, Inc., Memphis, Tenn.

[21] Appl. No.: 325,380

[22] PCT Filed: Apr. 28, 1993

[86] PCT No.: PCT/US93/03747

§ 371 Date: Oct. 26, 1994

§ 102(e) Date: Oct. 26, 1994

[87] PCT Pub. No.: WO93/21986

PCT Pub. Date: Nov. 11, 1993

Related U.S. Application Data

[63] Continuation of Ser. No. 874,887, Apr. 28, 1992, abandoned.

[51] Int. Cl.$^6$ ................................................. A61M 5/315
[52] U.S. Cl. ........................... 604/187; 604/218; 604/60
[58] Field of Search .................................... 604/187, 218, 604/192, 228, 193, 229, 219–220, 11, 15, 54–55, 57, 59, 60; 222/386

[56] References Cited

U.S. PATENT DOCUMENTS

| 282,144 | 7/1883 | Wortham . |
|---|---|---|
| D. 294,063 | 2/1988 | Smith . |
| 2,453,589 | 11/1948 | Poux . |
| 2,551,339 | 5/1951 | Ryan et al. . |
| 2,591,046 | 4/1952 | Brown . |
| 2,700,386 | 1/1955 | Ogle . |
| 2,724,385 | 11/1955 | Lockhart . |
| 2,725,057 | 11/1955 | Lockhart . |
| 2,832,340 | 4/1958 | Dann et al. . |
| 2,848,998 | 8/1958 | Bryan . |
| 2,879,766 | 3/1959 | Wilburn . |

(List continued on next page.)

FOREIGN PATENT DOCUMENTS

| 212506 | 7/1956 | Australia . |
|---|---|---|
| 241680 | 8/1965 | Australia . |
| 515007 | 7/1954 | Belgium . |
| 0302248 | 2/1989 | European Pat. Off. . |
| 1600637 | 9/1970 | France . |
| 360168 | 3/1962 | Switzerland . |
| 620824 | 3/1949 | United Kingdom . |

*Primary Examiner*—C. Fred Rosenbaum
*Assistant Examiner*—Perry E. Van Over
*Attorney, Agent, or Firm*—Robert A. Franks; Thomas D. Hoffman; Eric S. Dicker

[57] ABSTRACT

An applicator 10 includes a barrel 12 for containing a semisolid medicinal, the barrel including a large diameter cylindrical section 16, a small diameter cylindrical section 18 and an annular sloped transition section 20 that connects the large diameter cylindrical section and the small diameter cylindrical section, the sections being coaxial with each other, the small diameter cylindrical section including an inner surface defining an internal cavity for containing the medicinal, a first end 30 with a first opening 32 and equiangularly spaced, axially aligned evacuation channels 28 in the inner surface for venting air out of the barrel when the internal cavity is filled with the medicinal, and the large diameter cylindrical section includes a second opposite end with a second opening 24; a rubber plunger 58 for pushing the medicinal through the first opening, the plunger being slidably positioned in sealing contact with the inner surface of the small diameter cylindrical section; a plunger rod 86 connected with the plunger and contained within the barrel; a removable cap 40 for sealingly closing off the first opening and for applying a pushing force to the plunger rod when the cap is removed from the sealing relationship with the barrel in order to slidably move the plunger in the small diameter cylindrical section of the barrel to expel the medicinal from the first opening; and a connection assembly 36 for removably connecting the cap to the barrel such that the cap sealingly closes off the first opening. The applicator is useful for introducing medicinals into body cavities.

28 Claims, 7 Drawing Sheets

U.S. PATENT DOCUMENTS

| | | |
|---|---|---|
| 3,086,527 | 4/1963 | Forrest . |
| 3,108,591 | 10/1963 | Kolbas . |
| 3,128,765 | 4/1964 | Tint . |
| 3,506,008 | 4/1970 | Huck . |
| 3,677,245 | 7/1972 | Welch . |
| 3,747,479 | 7/1973 | Nightingale et al. . |
| 3,882,866 | 5/1975 | Zackheim . |
| 3,985,122 | 10/1976 | Topham . |
| 4,492,576 | 1/1985 | Dragan . |
| 4,636,202 | 1/1987 | Lowin et al. . |
| 4,911,695 | 3/1990 | Lindner . |
| 4,923,443 | 5/1990 | Greenwood et al. . |
| 4,932,941 | 6/1990 | Min et al. . |
| 4,952,208 | 8/1990 | Lix . |
| 4,997,371 | 3/1991 | Fischer . |
| 4,997,423 | 3/1991 | Okuda et al. . |
| 5,007,904 | 4/1991 | Densmore et al. . |
| 5,045,058 | 9/1991 | Demetrakopoulos . |

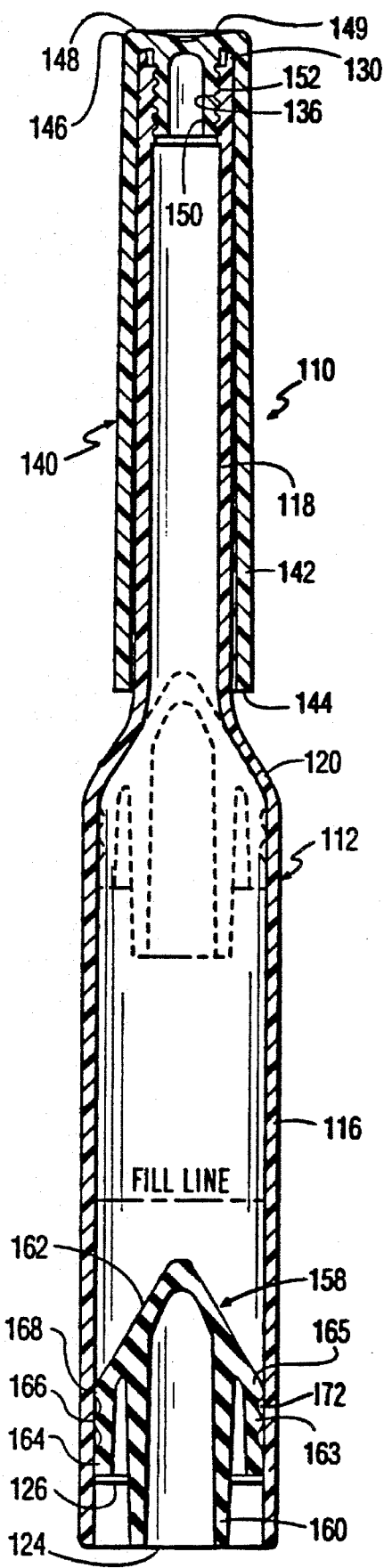
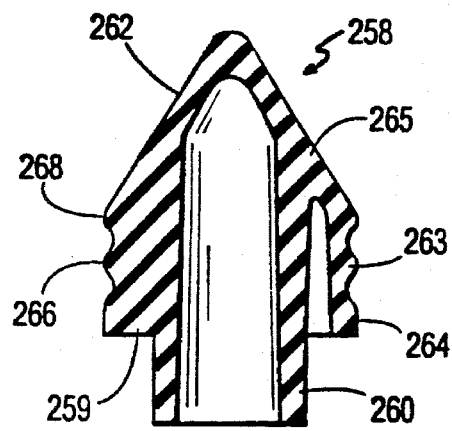
FIG. 17
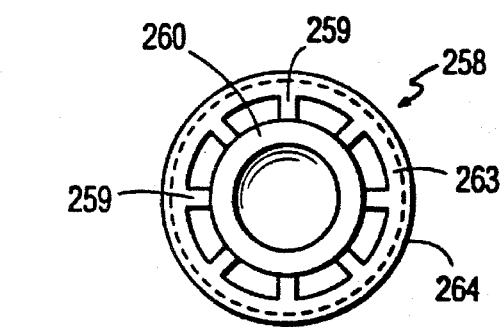
FIG. 18
FIG. 16

APPLICATOR FOR SEMISOLID MEDICATIONS

The present application is the United States national application corresponding to International Application No. PCT/US 93/03747, filed Apr. 28, 1993 and designating the United States, which PCT application is in turn a continuation of U.S. application Ser. No. 07/874,887, filed Apr. 28, 1992 now abandoned, the benefit of which applications are claimed pursuant to the provisions of 35 U.S.C. 120,363 and 365 (C).

INTRODUCTION TO THE INVENTION

The present invention relates generally to portable dispensing devices and, more particularly, is directed to a prefilled applicator for dispensing semisolid medication into body cavities.

The use of vaginal applicators to dispense medication is known in the art. For example, Schering-Plough HealthCare Products, Inc. of Memphis, Tenn. supplies an empty vaginal applicator with containers of its antifungal vaginal cream sold under its registered trademark "GYNE-LOTRIMIN". Specifically, the vaginal applicator includes an elongated small diameter cylindrical barrel and a plunger rod having one end thereof slidably fitted through one end of the barrel. The opposite end of the barrel has internal threads thereat.

In use, with the plunger rod retracted to its maximum extent, a tube of the vaginal cream is threaded into the threaded open end of the barrel and the opposite end of the tube is squeezed, forcing the cream into the barrel. Then, the tube is unscrewed from the barrel. The open end of the filled applicator is then inserted into the vagina as deeply as it will go comfortably. The plunger rod is then depressed until it stops. However, this procedure requires the user to fill the applicator prior to each use, which may become burdensome and messy. Further, since the user must fill the barrel herself, it is possible that she may not always supply the correct amount of cream into the barrel.

In this regard, single use, prefilled vaginal applicators have been sold, for example, by Ortho Pharmaceutical Corp. of Raritan, N.J. (also known as Advanced Care Products and related to Johnson & Johnson) under the trademark "CONCEPTROL", and by Columbia Laboratories, Inc. of Miami, Fla. under the trademark "REPLENS". The Ortho Pharmaceutical Corp. vaginal applicator is used for dispensing a contraceptive gel, while the Columbia Laboratories, Inc. vaginal applicator is used for dispensing a moisture replenisher.

These two applicators are virtually identical in construction, and include a barrel or applicator body, a twist off cap and a rubber plunger contained entirely inside of the barrel at all times. The barrel has a large diameter cylindrical section which tapers down to a small diameter cylindrical section through a smooth sloped transition section. The free end of the small diameter cylindrical section has internal threads thereat.

The twist off cap is formed by a cylindrical body with an open end and a closed end. There are ridges extending on the exterior surface of the cylindrical body in the longitudinal direction thereof, in order to aid the user in gripping the cap. In addition, at the closed end, there is an internal cylindrical boss extending inwardly of the cylindrical body. The outer diameter of the post is also provided with threads.

The inner diameter of the cylindrical body of the cap is larger than the outer diameter of the small diameter cylindrical section of the barrel so as to fit thereover, and the outer diameter of the boss is less than the inner diameter of the small diameter cylindrical section so as to fit therein. In such case, the external threads of the boss are threadedly engaged with the inner threads of the small diameter cylindrical section of the barrel, in order to removably secure the cap on the small diameter cylindrical section.

A cream, gel or the like is deposited in the small diameter cylindrical section, the transition section and a portion of the large diameter cylindrical section of the barrel. Thus, when the small diameter cylindrical section is positioned within the vagina, the plunger, which is positioned in the distal or free end of the large diameter cylindrical section is pushed toward the small diameter cylindrical section so as to push the cream, gel or the like into the vagina.

The rubber plunger includes a small diameter portion, a large diameter portion connected therewith at an annular shoulder, and a conical portion connected to the opposite end of the large diameter portion, the conical portion terminating in a rounded end. In addition, the large diameter portion is formed with annular ring-like protrusions or beads as part of the rubber material.

In use, after the cap is removed, the small diameter cylindrical section of the barrel is positioned within the vagina. Then, the open end of the cap is inserted within the large diameter cylindrical section and pushed against the annular shoulder which separates the small diameter portion of the plunger from the large diameter portion thereof. As a result, the plunger moves towards the small diameter cylindrical section of the barrel, thereby pushing out the cream, gel or the like into the vagina. Because the plunger is made of a rubber material, it seals against the inner wall of the barrel to prevent the escape of cream, gel or the like behind it.

However, the plunger is movable only in the large diameter cylindrical section. This means that some of the materials in the small diameter cylindrical section of the barrel will not be dispensed. Further, in order to fill the barrel with materials, the cap is removed, and the plunger is inserted within the barrel to the desired location. Then, the opening in the small diameter cylindrical section of the barrel is placed adjacent a filling port which fills the small diameter cylindrical section with the materials. This operation is disadvantageous since the cap must then be threaded onto the small diameter cylindrical section with the materials filled therein. In addition, a solid rubber plunger must be used in order to ensure that the beads thereof seal against the inner wall of the larger diameter cylindrical section, thereby requiring additional rubber material to be used.

A device constructed similarly to the above-discussed vaginal applicators sold by Ortho Pharmaceutical Corp. and Columbia Laboratories, Inc., is shown and disclosed in U.S. Pat. No. 3,506,008 to Huck. This patent discloses a medical applicator for insertion into a body cavity in order to dispense a medicament therein, and particularly discloses use of the same with respect to a vaginal cream. In Huck, the plunger is movable only in the large diameter section of the barrel, in the same manner as the vaginal applicators sold by Ortho Pharmaceutical Corp. and Columbia Laboratories, Inc. However, Huck provides the addition of an extension plug to the plunger, which extends into the small diameter cylindrical section of the barrel when the plunger is pushed in during use. The extension plug does not, however, extend to the opening of the small diameter cylindrical section of the barrel, so that some of the materials in the small diameter section will not be dispensed.

In addition, various other dispensing devices are known in the art.

For example, U.S. Pat. No. 3,086,527 to Forrest discloses a medical applicator particularly adapted to administer liquid cleansing agents and medicated solutions into the vagina. With this patent, a cylindrical sleeve or barrel has a slidable disc-shaped handle attachment with a central core rod connected axially thereto. A plug or tampon formed of a highly absorbent material is supported on the central core rod within the sleeve. A separate cylindrical pusher rod, having a knurled outer surface for traction and rotation, is provided which threadedly engages on the exposed side of the disc-shaped handle attachment in order to push the disc-shaped handle attachment, and thereby the plug, out of the sleeve, into the vagina. However, this device requires the use of a plug or tampon to hold the medication or other solution, rather than sealing a fluid in the sleeve or cylinder with a plunger.

Of a similar nature is U.S. Pat. No. 5,045,058 to Demetrakopoulos which relates to an apparatus for the cleansing and antisepsis of the vagina, and provides a phallic-shaped solid soap material.

U.S. Pat. No. 2,832,340 to Dann et al, although not relating to a vaginal applicator, discloses a syringe assembly having a syringe barrel for holding a liquid medicament, and a needle connected to the closed end thereof by a hub. The open end of the syringe barrel is closed by a slidable plunger made from a rubber or other elastomeric material. As with the above-discussed vaginal applicators by Ortho Pharmaceutical Corp. and Columbia Laboratories, Inc., this device uses a tubular push rod that has a two-fold function. First, the tubular push rod functions to cover the needle when not in use. Secondly, the tubular push rod has either a threaded bore or a threaded shaft for mating with a corresponding threaded shaft or threaded bore on the exposed side of the plunger.

U.S. Pat. No. 3,128,765 to Tint discloses a slight variation on Dann et al. The patent further teaches that the dispensing orifice need not be a needle. In all other relevant respects, this patent is the same as Dann et al.

U.S. Pat. No. 3,108,591 to Kolbas discloses a syringe of a similar type to Dann et al. The syringe includes a syringe barrel for holding a liquid medicament, and a needle connected to the closed end thereof. The open end of the syringe barrel is closed by a slidable plunger made from a rubber or other elastomeric material. As with the above-described Ortho and Columbia vaginal applicators, this device uses a tubular push rod. However, there is a variation with this device. Specifically, there is an ampule inserted within the barrel, rearwardly of the diluent therein, and which contains a powder medicament therein. The ampule is formed by an open-ended tube, the aforementioned plunger which closes off the inner end of the tube and which is also in sealing relation to the inner surface of the barrel, and a stopper which closes off the opposite end of the ampule. The exposed surface of the stopper has a threaded recess therein. There is also a cap which has a threaded hub at the closed end thereof. The cap serves a two-fold function, namely to cover the needle when not in use, and for mating with a corresponding threaded recess on the stopper.

The operation differs somewhat from the above-described Ortho and Columbia vaginal applicators because of the ampule. In use, the rear end of the open-ended rod is engaged by the palm of the user's hand and forced inwardly. As a result, the plunger is forced inwardly by the rod, whereby the diluent enters the ampule through a hole in the needle and mixes with the powder medicament therein. Thereupon, the cap is removed and secured to the stopper to push the same inwardly of the open-ended rod, and thereby force the mixture out of the needle.

As with the Ortho and Columbia vaginal applicators, the plunger of Kolbas has an enlarged head portion which engages the inner surface of the barrel, and a small diameter cylindrical stem portion integrally formed therewith. Accordingly, a shoulder is defined between the enlarged head portion and the stem portion. The open-ended rod is dimensioned with an inner diameter slightly less than the outer diameter of the stem portion of the plunger so as to fit thereover with a friction sealing fit, and the free end of the open-ended rod abuts against the shoulder. Further, the outer engaging surface of the enlarged head portion is formed with two axially spaced-apart annular beads or ridges which form a seal with the inner surface of the barrel.

U.S. Pat. No. 3,882,866 to Zackheim discloses a disposable enema syringe with a cannula cover which acts as the pusher for the plunger, in order to move the plunger against the contents in the barrel and thereby force the contents out of the cannula.

The difference between this patent and the aforementioned devices is primarily in the configuration of the plunger and the consequent use of the cannula cover in order to push the plunger through the barrel. Specifically, in this patent, the exteriorly-facing surface of the plunger is formed with a cruciform shaped wall, and the closed end of the cannula cover is formed on the outer surface thereof with an X-shaped opening which receives the cruciform shaped wall of the plunger therebetween in order to align the cannula cover with the plug.

However, with this device, the cruciform shaped wall is formed on the plunger itself, and extends to the entire diameter thereof. As a result, the cover/pusher has a complicated engaging structure in the form of the aforementioned X-shaped opening. Further, the cover/pusher engages a central, rather than peripheral, portion of the cruciform shaped wall. As a result, the there is little stability from tilting during the pushing operation.

U.S. Pat. No. 4,932,941 to Min et al is directed to a disposable syringe which cannot be reused. Unlike most of the aforementioned devices which only provide a rubber plunger in the barrel and use the cap for the dual purpose as a cover and as the plunger rod, this patent provides the plunger already mounted to one end of the plunger rod. However, the plunger and plunger rod are only slidable in the large diameter cylindrical section of the barrel. This means that some of the materials in the small diameter cylindrical section of the barrel will not be dispensed. It is also clear from the shape of the barrel that this device could not be used as a vaginal applicator. This is because of the small nozzle at the forward end of the barrel.

U.S. Pat. No. 4,997,423 to Okuda et al is directed to a laminated sliding stopper for a syringe, and it is similar in relevant respects to Min et al.

In both Min et al and Okuda et al, the package at the point of sale must be relatively large since the plunger rod extends out of the barrel by a substantial amount.

U.S. Pat. No. 2,591,046 to Brown discloses a hypodermic syringe assembly, which uses a screw-in arrangement of the cover/cap, similar to that found in previously discussed U.S. Pat. Nos. 2,832,340 to Dann et al, 3,108,591 to Kolbas and 3,128,765 to Tint. Brown, however, uses an inner piston closer to the needle and an outer piston closer to the wider open end of the large diameter cylindrical section of the barrel, the two pistons being movable in the large diameter cylindrical section of the barrel, and each having three ribs or rings in close proximity to each other, for the purpose of sealing. It is further noted that Brown has channels in the inner side wall of the large diameter cylindrical section of the barrel. The channels can be longitudinally or helically arranged. Further, the cap of Brown has a depression therein which receives the finger of the user when the cap is used to push the outer plunger inwardly of the barrel.

In basic operation, the diluent is contained between the two pistons, and the powder to be mixed therewith and then dispensed is found on the opposite side of the inner piston. The outer piston is first pushed inwardly. This results in the diluent pressure pushing the inner piston inwardly until the inner piston is positioned at the channels. Thereafter, continued pushing in of the outer piston forces the diluent through the channels and around the inner piston. This happens until the outer piston contacts the inner piston, whereby both pistons are pushed forward until the inner piston is in front of the channels so as to prevent escape of the diluent and powder. The diluent and powder are then mixed by shaking. Then, the outer piston is pushed all of the way in so as to expel the mixture through the syringe tip. However, the channels do not provide for the escape of air from the barrel during the pushing operation. This is because the abutted outer and inner pistons always provide a seal with the barrel to prevent the escape of the liquid mixture from the barrel at all times. Since the liquid mixture cannot escape rearwardly of the pistons, air can also not escape in this manner.

U.S. Pat. No. 4,911,695 to Lindner relates to a plunger for a power-driven angiographic syringe, and is provided merely to show a variation on the configuration of the plunger. The plunger is shown to include a distal conical portion and a generally cylindrical proximal portion having an outer surface with two axially spaced-apart annular ridges or beads bounding a groove therebetween.

U.S. Pat. No. 5,007,904 to Densmore et al is directed to a plunger for a power injector angiographic syringe, and has the same assignee as Lindner. The relevance of the patent is the same as Lindner.

U.S. Pat. No. 4,492,576 to Dragan is directed to a dental syringe and is relevant for the disclosure of the configuration of the plunger thereof. However, the device thereof is very different from a vaginal applicator and could not be used as such due to the spring loaded pusher for the plunger and the extraneous elements. Further, this device provides a venting chamber between the outer surface of the plunger and the inner surface of the barrel, with the plunger including a plurality of vent slots disposed on the end of plunger for venting the area to the rear of the plunger so as to create a vacuum behind the plunger. This effects a pull back of the plunger rod to relieve the back pressure of the material acting on the plunger upon the termination of an extruding operation, thereby preventing any drooling of the material from the cartridge. However, there is no venting of any air from the dental material itself during this operation.

U.S. Pat. No. 4,923,443 to Greenwood et al is directed to a hypodermic syringe. In Greenwood et al, the plunger has an internal cavity, and a beam plate having two fracturable elements is connected thereto. Further, the pusher or driver has a retractor head and a pusher head. During the pushing operation, the pusher head pushes the plunger into the barrel. During this time, the retractor head breaks the seal of the fracturable elements and enters the cavity of the plunger. During retraction, the retraction head engages the fracturable elements to withdraw the plunger.

U.S. Pat. No. 4,997,371 to Fischer is directed to a dental agent applicator. However, it requires the use of a curved applicator tip and bristles which form a brush in the applicator tip.

SUMMARY OF THE INVENTION

In accordance with an aspect of the present invention, an applicator includes barrel means for containing a medicinal, the barrel means including an inner surface defining an internal cavity for containing the medicinal, a first end with a first opening in communication with the internal cavity, a second opposite end with a second opening in communication with the internal cavity, and evacuation channel means for venting air out of the barrel means when the internal cavity is filled with the medicinal, the evacuation channel means being formed on the inner surface; plunger means for pushing the medicinal through the first opening, the plunger means being slidably positioned in the barrel means in sealing contact with the inner surface thereof; removable cap means for sealingly closing off the first opening and for applying a pushing force to the plunger means when the cap means is removed from the sealing relationship with the barrel means in order to slidably move the plunger means in the barrel means to expel the medicinal from the first opening, the cap means including an open end; and connection means for removably connecting the cap means to the barrel means such that the cap means sealingly closes off the first opening.

In accordance with another aspect of the present invention, an applicator includes barrel means for containing a medicinal, the barrel means including an inner surface defining an internal cavity for containing the medicinal, a first end with a first opening in communication with the internal cavity, a second opposite end with a second opening in communication with the internal cavity; plunger means for pushing the medicinal through the first opening, the plunger means being slidably positioned in the barrel means in sealing contact with the inner surface thereof, the plunger means including a cylindrical section, annular sealing flange means for sealing the plunger means against the inner surface of the barrel means, and securing means for securing the annular sealing flange means in surrounding and spaced relation to the cylindrical section; removable cap means for sealingly closing off the first opening, and for applying an axial pushing force to the plunger means when the cap means is removed from the sealing relationship with the barrel means in order to slidably move the plunger means in the barrel means to expel the medicinal from the first opening, and for applying an outwardly radial pressing force on the annular sealing flange means to press the annular sealing flange means into sealing contact with the inner surface of the barrel means, the cap means fitting between the cylindrical section and the annular sealing flange means to apply the radial pressing force on the annular sealing flange means; and connection means for removably connecting the cap means to the barrel means such that the cap means sealingly closes off the first opening.

In accordance with still another aspect of the present invention, an applicator includes barrel means for containing a medicinal, the barrel means including an inner surface defining an internal cavity for containing the medicinal, a first end with a first opening in communication with the internal cavity, a second opposite end with a second opening in communication with the internal cavity, plunger means for pushing the medicinal through the first opening, the plunger means being slidably positioned in the barrel means in sealing contact with the inner surface thereof, the plunger means including a cylindrical section, annular sealing flange means for sealing the plunger means against the inner surface of the barrel means, and rib means for securing the annular sealing flange means in surrounding and spaced relation to the cylindrical section and for substantially preventing inward radial deformation of the annular sealing flange means when the medicinal is expelled from the barrel means; removable cap means for sealingly closing off the first opening and for applying an axial pushing force to the plunger means when the cap means is removed from the sealing relationship with the barrel means in order to slidably move the plunger means in the barrel means to expel the medicinal from the first opening; and connection means for removably connecting the cap means to the barrel means such that the cap means sealingly closes off the first opening.

The above and other features of the invention will become readily apparent from the following detailed description thereof, which is to be read in connection with the accompanying drawings.

BRIEF DESCRIPTION OF THE DRAWINGS

FIG. 16 is a longitudinal cross-sectional view of an assembled applicator according to another embodiment of the present invention;

FIG. 17 is a longitudinal cross-sectional view of a plunger according to another embodiment of the present invention that can be used with the applicator of FIG. 16; and FIG. 18 is a bottom plan view of the plunger of FIG. 17.

DETAILED DESCRIPTION OF THE INVENTION

Figure 1:
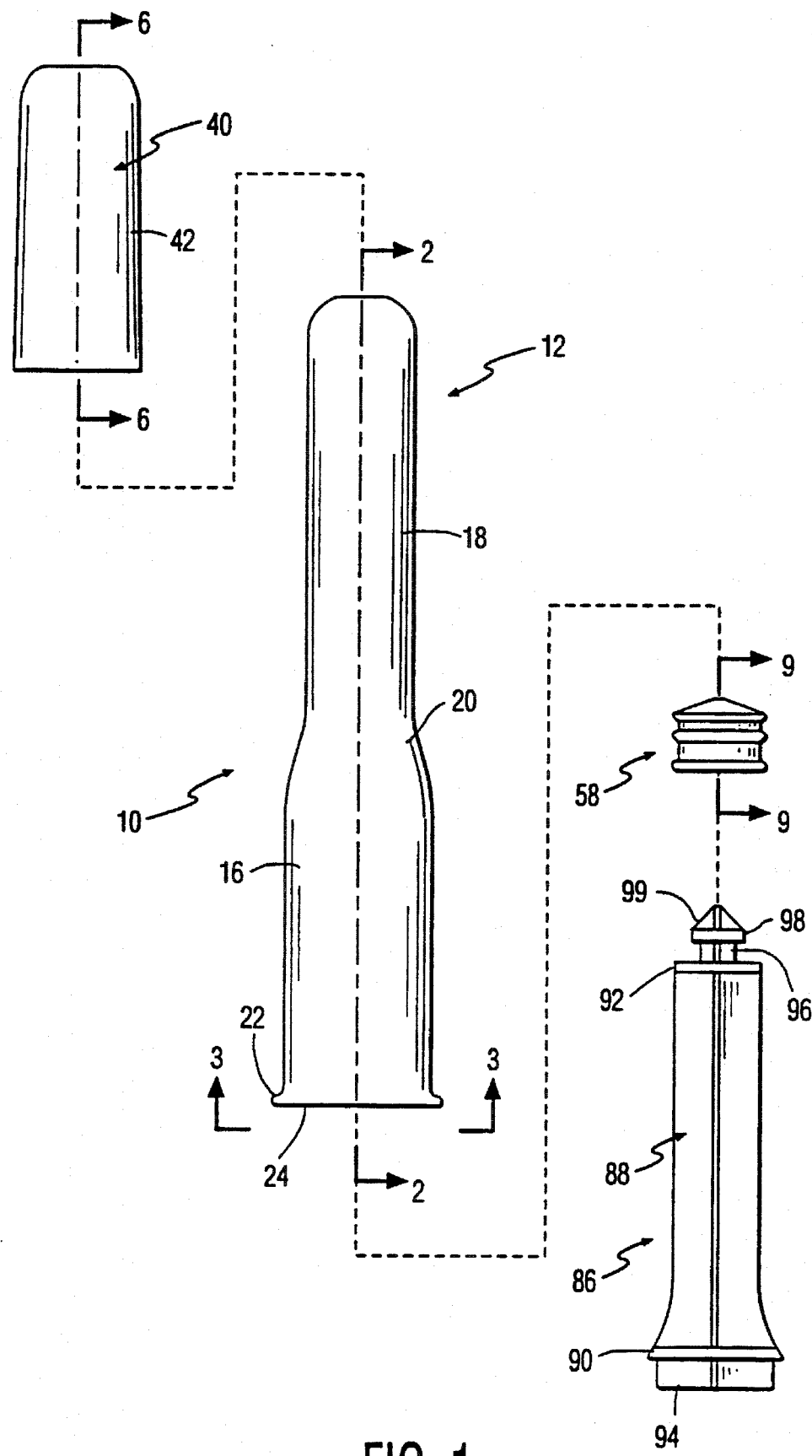
FIG. 1 is an exploded elevational view of the various parts of an applicator according to a first embodiment of the present invention.

The present invention is adapted to the dispensing of semisolid medicinals into body cavities. It is particularly useful for treating disorders of the vagina or rectum, when it is desired to apply medication directly to an injured or diseased site, or when it is desired to have a particular medication absorbed into blood vessels serving the vagina or rectum for achieving systemic effects while minimizing decomposition in the digestive, hepatic or other systems.

Description of the invention will be made with reference to certain presently preferred vaginal applicators. However, those having skill in the art will be aware that the invention is readily adapted to other uses by making appropriate dimensional changes for a particular body cavity and medication volume. Semisolid medicinals suitable for use with the device of this invention include creams, gels, ointments and the like, which exhibit fluid flow when pressure is applied.

Materials of construction will be chosen for compatibility with body tissues and fluids, and the medication formulation which is being dispensed, as well as for ease of fabrication, economy, structural strength and the like. In general, components which require rigidity will preferably be fabricated from thermoplastics such as polyolefins, including polypropylene, which is fairly inert, inexpensive and easily molded. Elastomeric components will frequently be natural rubber, butyl rubber or silicone rubber; stability of each elastomer candidate usually must be determined for contact with the exact medicinal formulation to be dispensed. The present invention is not limited to any specific materials of construction, the above-described materials being merely representative of those which are useful for use with certain formulations of medication.

Referring to the drawings in detail, and initially to FIGS. 1–5 thereof, a vaginal applicator 10 according to one embodiment of the present invention includes a hollow barrel 12 for containing a medicinal, such as the antifungal vaginal cream sold by Schering-Plough HealthCare Products, Inc. of Memphis, Tenn. under its registered trademark "GYNE-LOTRIMIN". Barrel 12 is preferably made from a relatively rigid plastic material that is compatible with bodily fluids and with the medicinal contained therein.

Barrel 12 is formed by large diameter cylindrical section 16 that tapers down to a small diameter cylindrical section 18 through an annular sloped transition section 20. Sections 16, 18 and 20 are formed coaxially and integrally with each other. As an example of dimensions thereof, large diameter cylindrical section 16 can have an outer diameter of approximately 2.37 cm (0.934 inch) and a height of approximately 4.78 cm (1.882 inches); small diameter cylindrical section 18 can have an outer diameter of approximately 1.69 cm (0.666 inch), an inner diameter of approximately 1.44 cm (0.566 inch) and a height of approximately 6.66 cm (2.622 inches); and transition section 20 can have a height of approximately 1.76 cm (0.691 inch); with the thickness of the wall forming each section preferably being no greater than approximately 2.5 mm (0.10 inch).

A radially outwardly extending annular flange 22 is formed on the outer surface of large diameter cylindrical section 16, at the lower open end 24 thereof, and forms a finger hold during the operation of expelling the vaginal cream from barrel 12, as will be described in greater detail hereinafter.

In addition, a pair of diametrically opposite retention beads 26 are formed on the inner surface of large diameter cylindrical section 16, and spaced approximately 6.5 mm (0.254 inch) from lower open end 24 thereof. As shown best in FIGS. 2 and 3, each retention bead 26 extends for approximately 90° around the circumference of large diameter cylindrical section 16. Further, each retention bead preferably has a radius of approximately 2.3 mm (0.09 inch) and thereby extends from the inner surface of large diameter cylindrical section 16 by this amount, although each retention bead 26 tapers at its extreme ends.

In accordance with an important aspect of the present invention, evacuation channels 28 are formed in the inner surface of small diameter cylindrical section 18. As shown best in FIGS. 2–4, there are four equiangularly arranged evacuation channels 28, although this number may vary within the scope of the present invention. Evacuation channels 28 extend in the axial direction of barrel 12, starting at approximately the junction between small diameter cylindrical section 18 and transition section 20, and extending for a height of approximately 1.35 cm (0.530 inch). Each evacuation channel 28 thereby forms a cut-out section from the inner wall of small diameter cylindrical section 18, with the cut-out being approximately 0.2 mm (0.008 inch) deep and approximately 1.6 mm (0.062 inch) wide.

As will be understood from the discussion hereinafter, evacuation channels 28 have been constructed inside small diameter cylindrical section 18 of barrel 12 to help vent out air during the filling of vaginal cream thereinto, which filling operation occurs from lower open end 24.

Figure 2:
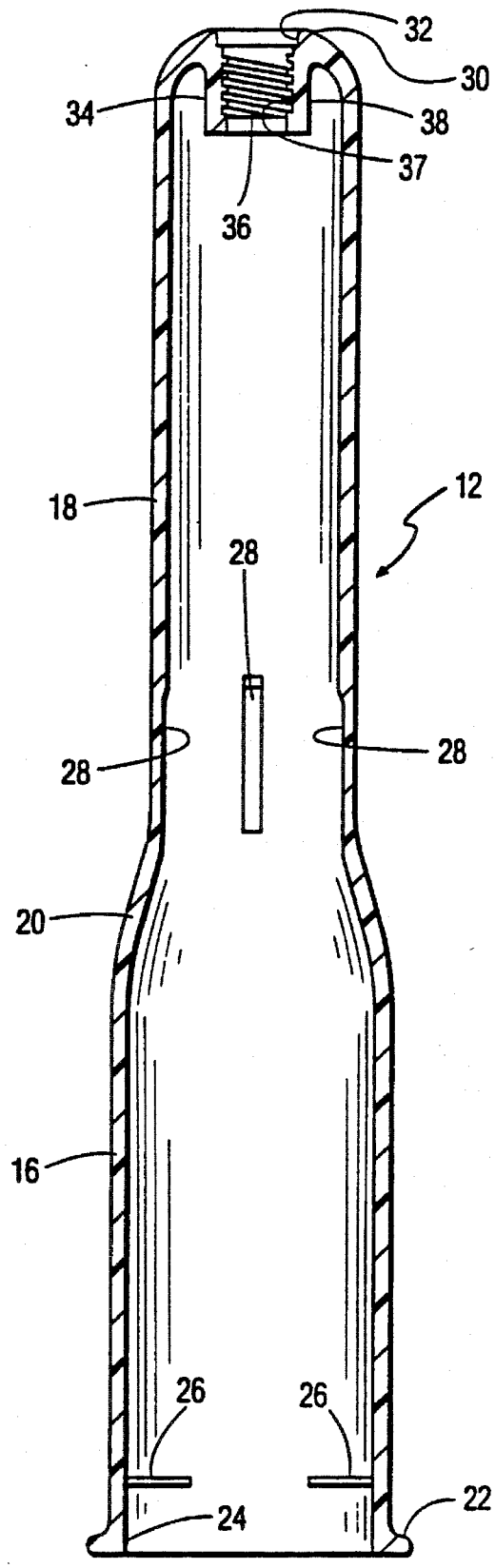
FIG. 2 is a cross-sectional view of the barrel of FIG. 1, taken along line 2—2 thereof.
Figure 3:
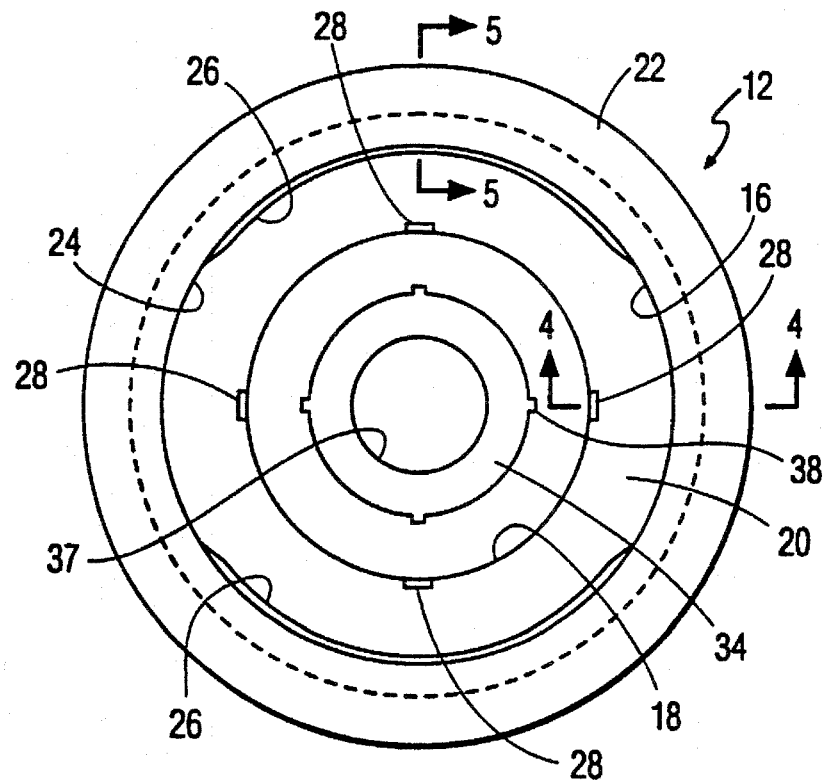
FIG. 3 is a bottom plan view of the barrel of FIG. 1, viewed along line 3—3 thereof.
Figure 5:
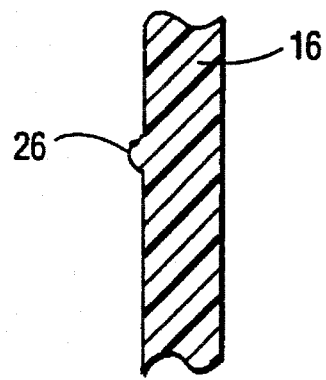
FIG. 5 is a cross-sectional view of the barrel of FIG. 3, taken along line 5—5 thereof, showing a lower retention bead.
Figure 4:
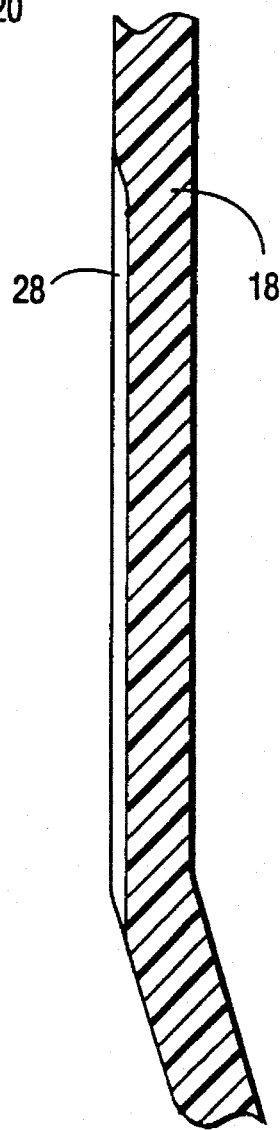
FIG. 4 is a cross-sectional view of the barrel of FIG. 3, taken along line 4—4 thereof, showing the venting channels.

As shown best in FIG. 2, the free end 30 of small diameter cylindrical section 18 reduces in diameter to a substantially rounded end, and is formed with a central axial bore 32 therethrough. An inner annular boss 34 is integrally formed with free end 30 and extends within small diameter cylindrical section 18 in axial alignment therewith. Boss 34 is formed with an inner bore 37 and internal threads 36 in the wall defining inner bore 37. In addition, inner annular boss 34 is formed with a plurality of equiangularly spaced unscrewing ribs 38 for removing barrel 12 from a mold after barrel 12 is formed. Preferably, boss 34 has a height of approximately 8.6 mm (0.340 inch) from free end 30 of small diameter cylindrical section 18 and has an internal diameter of approximately 6.4 mm (0.253 inch) and an internal thread diameter of approximately 5.8 mm (0.227 inch).

Referring now to FIGS. 1 and 6–8, vaginal applicator 10 further includes a cap 40 that serves a two-fold purpose. First, cap 40 functions to sealingly close off central axial bore 32, and secondly, cap 40 functions as a plunger pusher, as will be described in greater detail hereinafter. Cap 40 can be made from the same plastic material as barrel 12, or any other rigid materials.

Figure 6:
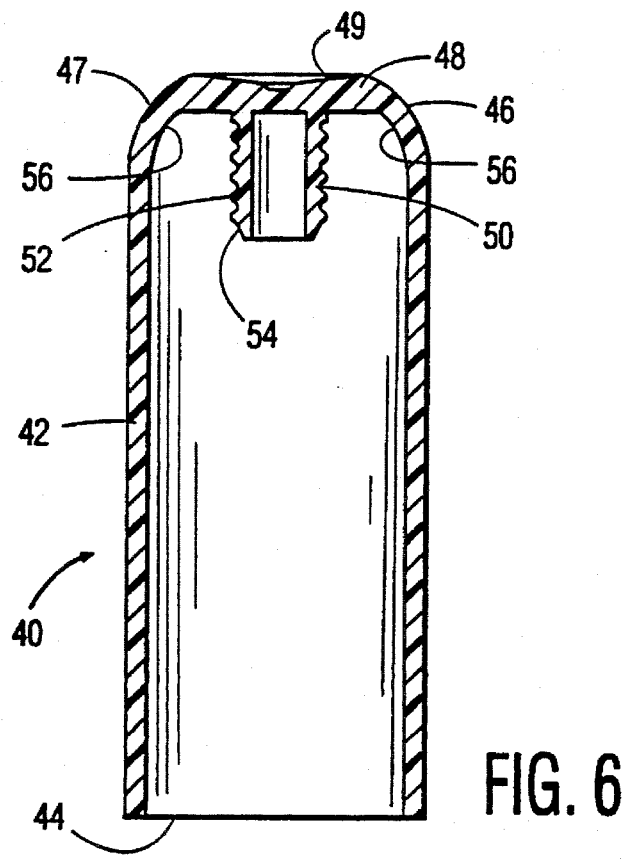
FIG. 6 is cross-sectional view of the cap of FIG. 1, taken along line 6—6 thereof.
Figure 7:
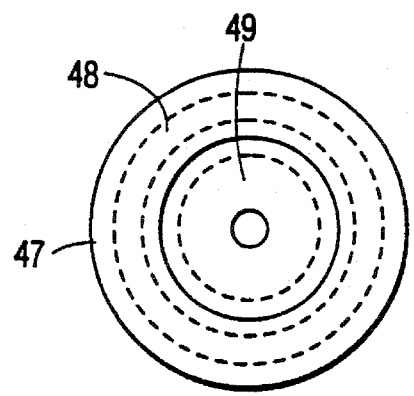
FIG. 7 is a top plan view of the cap of FIG. 6.
Figure 8:
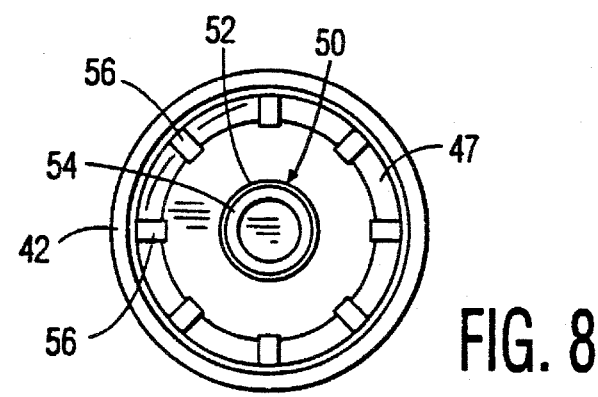
FIG. 8 is a bottom plan view of the cap of FIG. 6.

Cap 40 includes a generally cylindrical main body 42 that is open at one end 44 and closed at the opposite end 46 thereof by a circular top wall 48. As shown in FIG. 6, main body 42 is slightly rounded near opposite end 46 thereof by means of an inturned annular wall 47. Further, the outer surface of circular top wall 48 is provided with a part-spherical indent 49 which is adapted to receive the finger of a person using the vaginal applicator 10 during the pushing operation, as will be described hereinafter. Preferably, main body 42 has an inner diameter of approximately 1.80 cm (0.707 inch), a height of approximately 4.60 cm (1.811 inch) and a wall thickness of approximately 1.1 mm (0.045 inch). In this manner, cap 40 will fit over small diameter cylindrical section 18 with a clearance therebetween.

Cap 40 further includes a cylindrical internal boss 50 which extends inwardly from the inner surface of circular top wall 48, with internal boss 50 being coaxially arranged with respect to main body 42. Internal boss 50 has external threads 52 on the outer surface thereof which threadedly engage with internal threads 36 when internal boss 50 is fitted through central axial bore 32 and inner bore 37 of inner annular boss 34 of barrel 12. It will therefore be appreciated that the outer diameter of internal boss 50 is smaller than central axial bore 32 and inner bore 37. Preferably, internal bore 50 has an outer diameter of approximately 5.6 mm (0.221 inch) and an outer thread diameter of approximately 6.3 mm (0.247 inch). Accordingly, when cap 40 is threaded into inner annular bore 34 and connected with small diameter cylindrical section 18, an effective seal is provided which prevents the escape of the vaginal cream located within barrel 12. In order to aid the entry of internal bore 50 within central axial bore 32 and inner bore 37 of inner annular boss 34 of barrel 14, the free lower end of internal bore 50 is provided with a beveled annular edge 54.

Further, to aid in the sealing and securing capacity of cap 40, the inturned annular wall 47 of main body 42 at opposite end 46 thereof, is optionally provided with six equiangularly spaced unscrewing ribs 56. These ribs 56 deform slightly during the completion of the screwing of cap 40 onto small diameter cylindrical section 18, in order to provide a more secure connection therebetween.

Figure 9:
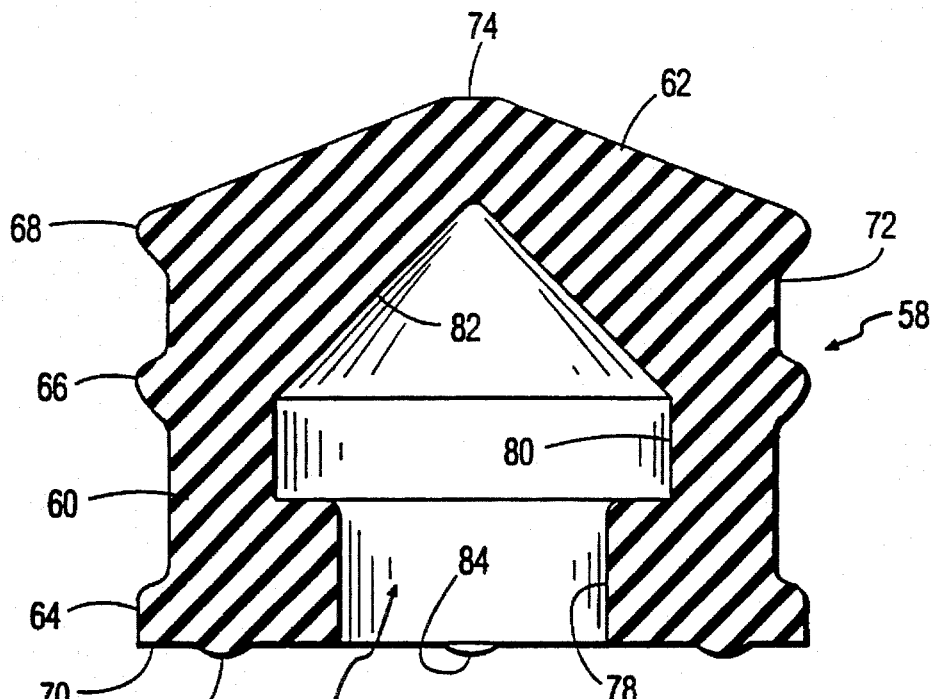
FIG. 9 is a cross-sectional view of the plunger of FIG. 1, taken along line 9—9 thereof.
Figure 10:
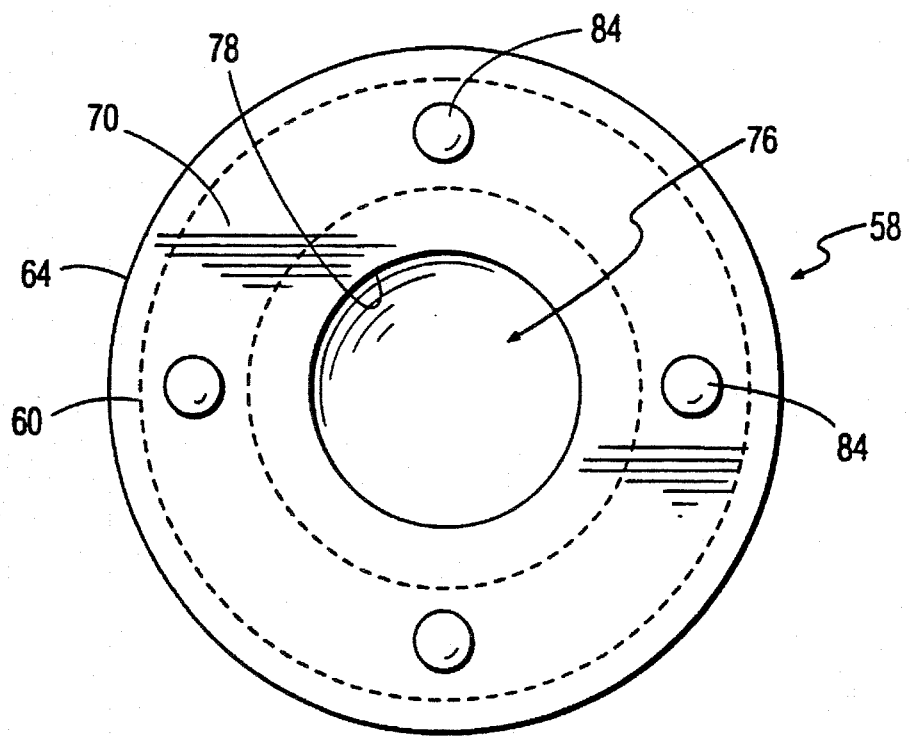
FIG. 10 is a bottom plan view of the plunger of FIG. 9.
Figure 11:
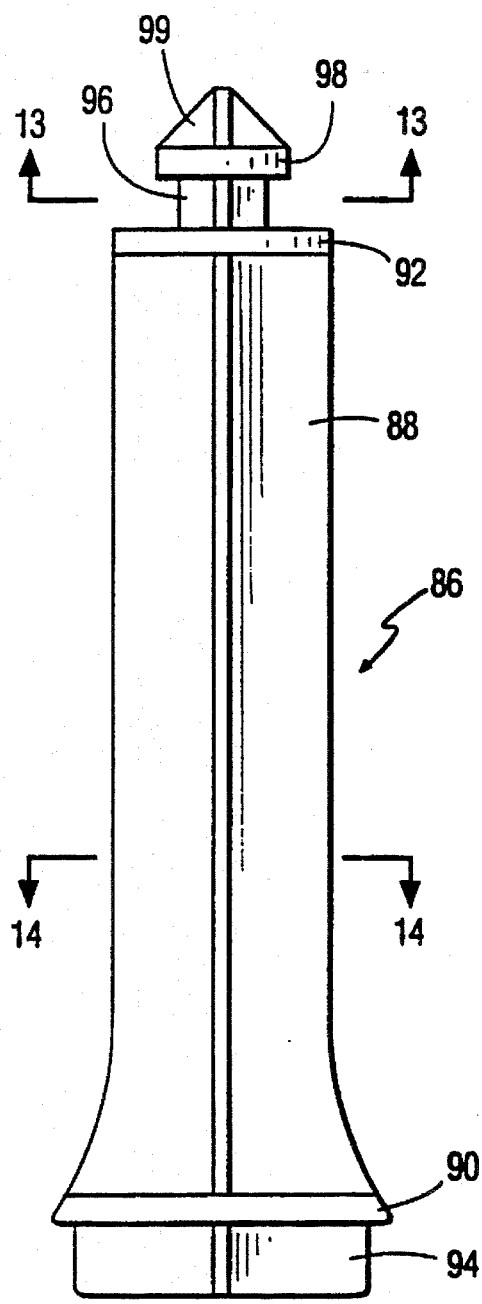
FIG. 11 is an enlarged elevational view of plunger rod of FIG. 1.
Figure 12:
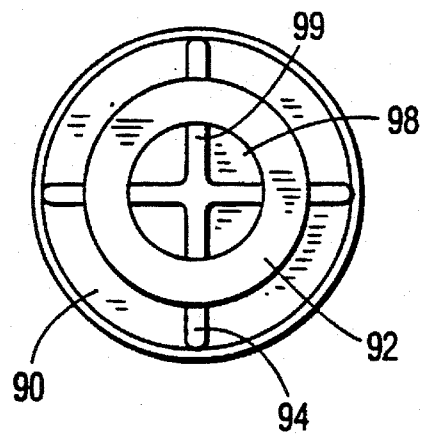
FIG. 12 is a top plan view of the plunger rod of FIG. 11.
Figure 13:
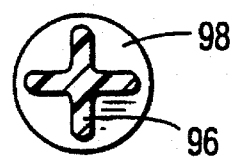
FIG. 13 is a cross-sectional view of the plunger rod of FIG. 11, taken along line 13—13 thereof.
Figure 14:
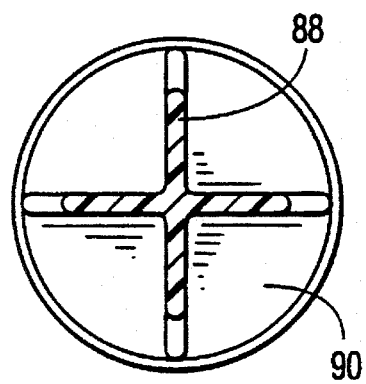
FIG. 14 is a cross-sectional view of the plunger rod of FIG. 11, taken along line 14—14 thereof.
Figure 15:
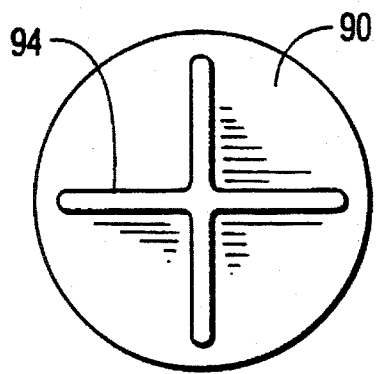
FIG. 15 is a bottom plan view of the plunger rod of FIG. 11.

Referring now to FIGS. 1, 9 and 10, vaginal applicator 10 further includes a plunger 58 that fits snugly within small diameter cylindrical section 18 of barrel 12. The plunger is fabricated from a resilient material, preferably an elastomer, and usually is a rubber. Plunger 58 includes a cylindrical section 60 integrally connected with a frusto-conical section 62. Preferably, cylindrical section 60 has an outer diameter of approximately 1.40 cm (0.552 inch) and a height of approximately 8.7 mm (0.343 inch). Further, cylindrical section 60 includes three annular beads 64, 66 and 68 integrally formed on the outer surface thereof. The lower annular bead 64 is formed at the lower end 70 of cylindrical section 60 and preferably has a height of approximately 0.89 mm (0.035 inch) and an outer diameter of approximately 1.46 cm (0.576 inch); the intermediate annular bead 66 is formed at a distance of approximately 4.6 mm (0.183 inch) from lower end 70 and preferably has an outer diameter of approximately 1.48 cm (0.582 inch); and the upper annular bead 68 is formed at the opposite upper end 72 of cylindrical section 60 and preferably also has an outer diameter of approximately 1.48 cm (0.582 inch). Accordingly, since small diameter cylindrical section 18 has an inner diameter of approximately 1.44 cm (0.566 inch), annular beads 64, 66 and 68 deform against the inner surface of small diameter cylindrical section 18 to form an air tight seal therewith. At the same time, however, the outer diameters of annular beads 64, 66 and 68 are not too large, thereby permitting sliding movement of plunger 58 within Small diameter cylindrical section 18 of plunger 12.

Frusto-conical section 62 forms an extension of upper annular bead 68 and tapers from the outer diameter of upper end 72 of cylindrical section 60 to a lesser diameter flat circular end 74. Preferably, frusto-conical section 62 has a height of 2.2 mm (0.085 inch) from the upper end of cylindrical section 60, and lesser diameter circular end 74 has a diameter of approximately 1.3 mm (0.050 inch).

In addition, cylindrical section 60 includes an internal cavity 76 open at lower end 70 of cylindrical section 60, for receiving a plunger rod tip, as will be described hereinafter. Cavity 76 is formed first by a first cylindrical cavity section 78 which opens through lower end 70 and preferably has a diameter of approximately 5.7 mm (0.226 inch) and a height of approximately 2.9 mm (0.113 inch). Cavity 76 further includes a second cylindrical cavity section 80 which is in open communication with first cylindrical cavity section 78 and has a diameter of approximately 8.5 mm (0.336 inch)

and a height of approximately 2.3 mm (0.090 inch). Finally, cavity 76 includes a third conical cavity section 82 having its base in open communication with second cylindrical cavity section 80 and a having a base diameter of approximately 8.5 mm (0.336 inch), a height of approximately 4.1 mm (0.162 inch) and a side wall inclined at 45° with respect to lower end 70.

In addition, the lower end 70 of cylindrical section 60 includes four equiangularly spaced nubs 84 thereon, which preferably have a diameter of approximately 1.2 mm (0.047 inch), a height of approximately 0.25 mm (0.010 inch) and are spaced on a 1.09 cm (0.429 inch) diameter circle.

Finally, vaginal applicator 10 includes a plunger rod 86, usually formed of the same material as barrel 12 and cap 40 or another rigid material. Plunger rod 86 includes a cruciform shaped main body 88 centrally connected at its lower end to the upper surface of a lower circular disc 90 having an outer peripheral beveled edge, and centrally connected at its upper end to the lower surface of an upper circular disc 92. Preferably, lower circular disc 90 has a diameter of approximately 2.09 cm (0.822 inch) and a height of approximately 1.6 mm (0.062 inch), and upper circular disc 92 has a diameter of approximately 1.40 cm (0.551 inch) and a height of approximately 1.6 mm (0.062 inch). Cruciform shaped main body 88 has a diameter of approximately 1.40 cm (0.551 inch) for most of its length, but diverges outwardly at its extreme lower end to the diameter of lower circular disc 90. Preferably, the length of cruciform shaped main body 88 is approximately 5.95 cm (2.342 inch).

Plunger rod 86 further includes a cruciform shaped cap restraint 94 centrally formed on the lower surface of lower circular disc 90. Preferably, cap restraint 94 has a diameter of approximately 1.81 cm (0.712 inch) and a height of approximately 4.7 mm (0.187 inch). In this regard, it will be appreciated that the open end 44 of cap 40 has an inner diameter of approximately 1.80 cm (0.707 inch). In the preferred embodiment where plunger rod 86 and cap 40 are formed of a plastic material, open end 44 of cap 40 will fit over cap restraint 94 with a slight pressure fit. In this manner, cap 40 can serve in its pusher mode to push plunger rod 86 within barrel 12, while cap restraint 94 helps to stabilize cap 40 during such motion. Specifically, cruciform shaped cap restraint 94 provides an engagement for removable cap 40, while also preventing tilting of cap 40 during the pushing operation, thereby providing a broad base by which plunger 58 can be evenly and uniformly pushed. In other words, since cap restraint 94 does not extend to the entire outer diameter of the lower circular disc 90, cap 40 fits snugly around cruciform shaped cap restraint 94 and engages the outer surface of the lower circular disc 90 along an annular path to push plunger 58 inwardly of barrel 12.

A cruciform shaped neck 96 is centrally formed on the upper surface of upper circular disc 92. Preferably, neck 96 has a diameter of approximately 5.7 mm (0.223 inch) and a height of approximately 3.4 mm (0.135 inch). Finally, a circular securing disc 98 is centrally formed on the upper end of neck 96, and a cruciform shaped conical section 99 is formed on the upper surface of circular securing disc 98. Circular securing disc 98 preferably has a diameter of approximately 8.4 mm (0.332 inch) and a height of approximately 1.8 mm (0.070 inch), and conical section 99 preferably has a height of approximately 3.7 mm (0.144 inch) and a diameter at its base of approximately 8.4 mm (0.332 inch). In addition, each of the four cruciform webs which make up each of cruciform shaped main body 88, cruciform shaped cap restraint 94, cruciform shaped neck 96 and cruciform shaped conical section 99, preferably have a width of approximately 1.1 mm (0.045 inch).

In order to assemble the above elements, cruciform shaped neck 96, circular securing disc 98 and cruciform shaped conical section 99 are fit within internal cavity 76 of plunger 58. Specifically, cruciform shaped neck 96 fits within first cylindrical cavity section 78, circular securing disc 98 fits within second cylindrical cavity section 80 and cruciform shaped conical section 99 fits within third conical cavity section 82. Because plunger 58 is made from a non-rigid material, it readily deforms under applied pressure when cruciform shaped neck 96, circular securing disc 98 and cruciform shaped conical section 99 are force fit into internal cavity 76 thereof. In this manner, plunger 58 is mounted on top of plunger rod 86.

Then, cap 40 is threadedly secured to barrel 12. With barrel 12 inverted so that large diameter cylindrical section 16 is positioned above small diameter cylindrical section 18, a predetermined amount of the vaginal cream is dispensed through lower open end 24 of large diameter cylindrical section 16, into small diameter cylindrical section 18, from a dispensing tube, port or the like. Thereafter, the assembled plunger and plunger rod assembly is inserted through lower open end 24, into small diameter cylindrical section 18 to provide an air-tight space in small diameter cylindrical section 18 for the vaginal cream. Because cap 40 provides an effectively air-tight seal with small diameter cylindrical section 18, however, the air within small diameter cylindrical section 18 must be displaced somewhere. In accordance with the present invention, as plunger 58 is pushed inwardly, it passes over evacuation channels 28. This pushing operation forces air out of small diameter cylindrical section 18 through evacuation channels 28. When plunger 58 passes the upper extreme ends of evacuation channels 28, plunger 58 provides a seal to small diameter cylindrical section 18. At this time, however, all or substantially all of the air has already been evacuated from small diameter cylindrical section 18 so that the vaginal cream is stored in an air-tight, substantially air evacuated environment. It will be appreciated that, with this arrangement of the plunger and plunger rod combination which slidably extend through small diameter cylindrical section 18, plunger 58 and plunger rod 86 are always contained entirely in barrel 12, resulting in a decrease in overall length of vaginal applicator 10. In this regard, since plunger rod 86 does not extend at any time from barrel 12, the packaging for vaginal applicator 10 is reduced.

When it is desired to use vaginal applicator 10, cap 40 is removed and open end 44 thereof is inserted over cruciform shaped cap restraint 94 until open end 44 abuts against the lower surface of lower circular disc 90. Small diameter cylindrical section 18 is then inserted in the vagina. Thereafter, the user holds two fingers on radially outwardly extending annular flange 22 and puts a third finger on spherical indent 49 of circular top wall 48 of cap 40, and pushes inwardly, thereby expelling the vaginal cream from barrel 12 into the vagina.

Referring now to FIG. 16, a vaginal applicator 110 according to another embodiment of the present invention will now be described, in which elements corresponding to vaginal applicator 10 are identified by the same reference numerals incremented by 100, and a detailed description of the common elements (such as lower open end 124) will be omitted herein for the sake of brevity.

Vaginal applicator 110 includes a barrel 112 for containing the vaginal cream and is made from a relatively rigid plastic material that is compatible with bodily fluids and with the vaginal cream contained therein. Barrel 112 is formed by a large diameter cylindrical section 116 that tapers down to a small diameter cylindrical section 118 through an annular sloped transition section 120. Annular sections 116, 118 and 120 are formed coaxially and integrally with each other. As an example of dimensions thereof, large diameter cylindrical section 116 can have an outer diameter of approximately 1.97 cm (0.777 inch) and a height of approximately 5.96 cm (2.345 inches); small diameter cylindrical section 118 can have an outer diameter of approximately 9.8 mm (0.386 inch) and a height of approximately 5.96 cm (2.345 inches); and transition section 120 can have a height of approximately 1.89 cm (0.743 inch); with the thickness of the wall forming each section preferably being approximately 1.1 mm (0.045 inch).

In addition, an annular retention bead 126 is formed on the inner surface of large diameter cylindrical section 116, and spaced approximately 6.3 mm (0.25 inch) from lower open end 124 thereof. Retention bead 126 preferably has a radius of approximately 2.5 mm (0.10 inch) and thereby extends in a radially inward direction from the inner surface of large diameter cylindrical section 116 by this amount.

Further, the free end 130 of small diameter cylindrical section 118 is open, and the inner surface of small diameter cylindrical section 118 thereat, is formed with internal threads 136. Preferably, threads 136 extend for a distance of approximately 8.6 mm (0.340 inch) from free end 130 of small diameter cylindrical section 118.

Vaginal applicator 110 further includes a cap 140 that serves a two-fold purpose. First, cap 140 functions to sealingly close off open free end 130, and secondly, cap 140 functions as a plunger pusher, as will be described in greater detail hereinafter. Cap 140 is preferably made from the same plastic material as barrel 112.

Cap 140 includes a generally cylindrical main body 142 that is open at one end 144 and closed at the opposite end 146 thereof by a circular top wall 148. Further, the outer surface of circular top wall 148 is provided with a part-spherical indent 149 which is adapted to receive the finger of a person using vaginal applicator 110 during the pushing operation, as will be described hereinafter. Preferably, main body 142 has an inner diameter of approximately 1.06 cm (0.418 inch), a height of approximately 5.96 cm (2.345 inch) and a wall thickness of approximately 1.1 mm (0.045 inch). In this manner, cap 140 will fit over small diameter cylindrical section 118 with a clearance therebetween.

Cap 140 further includes a cylindrical internal boss 150 which extends inwardly from the inner surface of circular top wall 148, with internal boss 150 being coaxially arranged with respect to main body 142. Internal boss 150 has external threads 152 on the outer surface thereof which threadedly engage with internal threads 136 when internal boss 150 is fitted through open free end 130 of barrel 112. It will therefore be appreciated that the outer diameter of internal boss 150 is smaller than open free end 130. Preferably, internal boss 150 has an outer diameter which permits it to be received in small diameter cylindrical section 118 in threaded engagement with internal threads 136 thereof. Accordingly, when cap 140 is threaded into small diameter cylindrical section 118, an effective air-tight seal is provided which prevents the escape of the vaginal cream located within barrel 112.

Vaginal applicator 110 further includes a rubber plunger 158 that fits snugly within large diameter cylindrical section 116 of barrel 112. Plunger 158 includes a generally cylindrical section 160 integrally connected with a conical shell section 162. Preferably, cylindrical section 160 has an outer diameter of approximately 1.01 cm (0.398 inch), a height of approximately 1.45 cm (0.57 inch) and a thickness of approximately 3.1 mm (0.124 inch).

Conical shell section 162 tapers from upper end 172 of cylindrical section 160, and preferably has a height of approximately 1.26 cm (0.498 inch) from the upper end of cylindrical section 160.

In addition, and in accordance with another important aspect of the present invention, an annular sealing flange 163 is formed in partial surrounding and in spaced relation from cylindrical section 160 and is connected to the juncture of cylindrical section 160 and conical section 162 by an extension 165 of conical shell section 162. Annular sealing flange 163 has a height of approximately 8.0 mm (0.315 inch) and an outside diameter of approximately 1.68 cm (0.661 inch), and thereby forms a seal against the inner surface of large diameter cylindrical section 116 of barrel 112. In order to effectuate this seal, three annular beads 164, 166 and 166 are integrally formed on the outer surface of annular sealing flange 163. Since large diameter cylindrical section 116 has an inner diameter of approximately 1.65 cm (0.650 inch), annular beads 164, 166 and 168 deform against the inner surface of large diameter cylindrical section 116 to form an air tight seal therewith. At the same time, however, the outer diameters of annular beads 164, 166 and 168 are not too large, thereby permitting sliding movement of plunger 158 within large diameter cylindrical section 116 of plunger 112. It is noted that vaginal applicator 110 does not include a plunger rod, as with vaginal applicator 10 described above.

Unlike vaginal applicator 10, vaginal applicator 110 is filled through open free end 130 of small diameter cylindrical section 118 after plunger 158 has been fitted within large diameter cylindrical section 116. In such case, retention bead 126 retains plunger 158 within barrel 112. Thereafter, cap 140 is threaded onto barrel 112.

When it is desired to use vaginal applicator 110, cap 140 is removed and the open end 144 thereof is inserted over cylindrical section 160 and within the confines of annular sealing flange 163. In such case, cap 140 provides an outwardly radial force on annular sealing flange 163 in order to press annular sealing flange 163 against the inner surface of large diameter cylindrical section 116 in order to ensure a tight seal thereat. This prevents annular sealing flange 163 from buckling in a radial inward direction by the force of the vaginal cream thereon. Small diameter cylindrical section 118 is then inserted in the vagina. Thereafter, the user holds the outer surface of large diameter cylindrical section 116 and puts a third finger on spherical indent 149 of circular top wall 148 of cap 140, and pushes inwardly, thereby expelling the vaginal cream from barrel 112 into the vagina.

Referring now to FIG. 17 and FIG. 18, in accordance with another embodiment of the invention, a plunger 258 which can be used in vaginal applicator 110 will now be described, in which elements corresponding to plunger 158 are identified by the same numerals augmented by 100, and a detailed description of the common elements (such as annular beads 264, 266 and 268) will be omitted herein for the sake of brevity.

Basically, plunger 258 is identical with plunger 158 with the exception that radially directed ribs 259 are connected between cylindrical section 260 and annular sealing flange 263. Although eight ribs 259 are shown, it will be appreciated that the present invention is not limited thereby.

Accordingly, with plunger 258, the open free end 144 of cap 140 does not fit between cylindrical section 260 and annular sealing flange 263. Rather, open free end 144 abuts against the edges of ribs 259 in order to push plunger 258 inwardly. However, ribs 259 prevent annular sealing flange 263 from deforming in a radially inward direction in the presence of the force of the vaginal cream during the ejection operation.

Having described specific embodiments of the invention with reference to the accompanying drawings, it will be appreciated that the present invention is not limited to those precise embodiments and that various changes and modifications can be effected therein by one of ordinary skill in the art without departing from the scope or spirit of the invention as defined solely by the appended claims.

What is claimed is:

1. An applicator for introducing a semisolid medicinal into a body cavity, comprising:
   a) barrel means for containing the medicinal, said barrel means including:
      i) an inner surface defining an internal cavity for containing the medicinal,
      ii) a first end with a first opening in communication with said internal cavity,
      iii) a second opposite end with a second opening in communication with said internal cavity, and
      iv) evacuation channel means for venting air out of said barrel means when said internal cavity is filled with said medicinal, said evacuation channel means being formed on said inner surface;
   b) plunger means for pushing said medicinal through said first opening, said plunger means being slidably positioned in said barrel means in sealing contact with the inner surface thereof;
   c) removable cap means for sealingly closing off said first opening and for applying a pushing force to said plunger means when said cap means is removed from said sealing relationship with said barrel means in order to slidably move said plunger means in said barrel means to expel said medicinal from said first opening, said cap means including an open end; and
   d) connection means for removably connecting said cap means to said barrel means such that said cap means sealingly closes off said first opening.

2. The applicator according to claim 1, wherein said barrel means includes a large diameter cylindrical section, a small diameter cylindrical section and an annular sloped transition section that connects said large diameter cylindrical section and said small diameter cylindrical section, said large diameter cylindrical section, said small diameter cylindrical section and said annular sloped transition section being formed coaxially with each other.

3. The applicator according to claim 2, wherein said small diameter cylindrical section includes:
   a) a portion of said inner surface,
   b) said evacuation channel means for venting air out of said small diameter cylindrical section when said internal cavity is filled with said medicinal, said evacuation channel means being formed on said portion of said inner surface of said small diameter cylindrical section, and
   c) said first end with said first opening.

4. The applicator according to claim 3, wherein said evacuation channel means includes a plurality of elongated axially extending evacuation channels formed in said portion of the inner surface of said small diameter cylindrical section.

5. The applicator according to claim 4, wherein said evacuation channels are equiangularly arranged around said small diameter cylindrical section.

6. The applicator according to claim 3, wherein said evacuation channel means has a first end positioned at approximately a junction between said small diameter cylindrical section and said transition section, and extends in a direction toward said first opening in said small diameter cylindrical section.

7. The applicator according to claim 2, wherein said large diameter cylindrical section includes:
   a) said second opposite end,
   b) an outer surface, and
   c) finger holding means on said outer surface for restraining said barrel means during an operation when said medicinal is expelled from said first opening of said barrel means.

8. The applicator according to claim 1, further including plunger rod means, connected with said plunger means, for engaging with said cap means so that said cap means can apply a pushing force to said plunger means, through said plunger rod means, when said cap means is removed from said sealing relationship with said barrel means, in order to slidably move said plunger means in said barrel means to expel said medicinal from said first opening.

9. The applicator according to claim 8, wherein said plunger rod means includes a main body, tip means for connecting said plunger means thereto and cap restraint means for engaging with said cap means when said cap means is removed from said sealing connection with said barrel means.

10. The applicator according to claim 9, wherein said plunger rod means includes lower disc means connected to one end of said main body, and said cap restraint means has an outer diameter less than the outer diameter of said lower disc means, to provide an annular engaging surface on said lower disc means for engagement by said open end of said cap means.

11. The applicator according to claim 10, wherein said cap restraint means has a cruciform shape.

12. The applicator according to claim 10, wherein said barrel means includes a large diameter cylindrical section, a small diameter cylindrical section and an annular sloped transition section that connects said large diameter cylindrical section and said small diameter cylindrical section, said large diameter cylindrical section, said small diameter cylindrical section and said annular sloped transition section being formed coaxially with each other, said large diameter cylindrical section includes said second opposite end with said second opening, a portion of said inner surface, and retention bead means for engaging with said lower disc means to retain said plunger rod means in said large diameter cylindrical section, said retention bead means being formed on said portion of the inner surface of said large diameter cylindrical section in spaced relation from the second opposite end thereof.

13. The applicator according to claim 10, wherein said barrel means includes a large diameter cylindrical section, a small diameter cylindrical section and an annular sloped transition section that connects said large diameter cylindrical section and said small diameter cylindrical section, said large diameter cylindrical section, said small diameter cylindrical section and said annular sloped transition section being formed coaxially with each other, said plunger means being slidably positioned in said small diameter cylindrical section of said barrel means in sealing contact with the inner surface thereat, at least a portion of said main body being movable in said small diameter cylindrical section, and said lower disc means and said cap restraint means being movable only in said large diameter cylindrical section.

14. The applicator according to claim 9, wherein said plunger means includes a lower end and an internal cavity open at said lower end thereof for receiving said tip means of said plunger rod means therein, to secure said plunger means to said plunger rod means.

15. The applicator according to claim 8, wherein said plunger means and said plunger rod means are positioned in said barrel means at all times.

16. The applicator according to claim 1, wherein said connection means includes:
   a) an inner boss connected with said first end of said barrel means and extending within said barrel means, said inner boss having an annular wall defining an inner bore in axial alignment with said first opening, and internal threads in the annular wall; and
   b) an internal boss connected with said cap means and having external thread means for threaded engagement with the internal threads of said inner boss of said barrel means, to removably connect said cap means to said barrel means.

17. The applicator according to claim 1, wherein said cap means includes a generally cylindrical main body having opposite ends, with said one open end and an opposite end which is closed by a closure wall, said closure wall having indent means for receiving a finger of a person during an expelling operation when said medicinal is pushed out of said first opening of said barrel means.

18. The applicator according to claim 17, wherein said indent means has a part-spherical configuration.

19. The applicator according to claim 1, wherein said plunger means includes a cylindrical section and a frusto-conical section connected therewith, said cylindrical section including a plurality of annular bead means for providing a seal between said plunger means and the inner surface of said barrel means, while permitting sliding movement of said plunger means in said barrel means.

20. An applicator for introducing a semisold medicinal into a body cavity comprising:
   a) barrel means for containing the medicinal, said barrel means including:
      i) an inner surface defining an internal cavity for containing the medicinal,
      i) a first end with a first opening in communication with said internal cavity, and
      iii) a second opposite end with a second opening in communication with said internal cavity,
   b) plunger means for pushing said medicinal through said first opening, said plunger means being slidably positioned in said barrel means in sealing contact with the inner surface thereof, said plunger means including:
      i) a cylindrical section,
      ii) annular sealing flange means for sealing said plunger means against the inner surface of said barrel means, and
      iii) securing means for securing said annular sealing flange means in surrounding and spaced relation to said cylindrical section;
   c) removable cap means for sealingly closing off said first opening, for applying an axial pushing force to said plunger means when said cap means is removed from said sealing relationship with said barrel means in order to slidably move said plunger means in said barrel means to expel said medicinal from said first opening, and for applying an outwardly radial pressing force on said annular sealing flange means to press said annular sealing flange means into sealing contact with the inner surface of said barrel means, said cap means fitting between said cylindrical section and said annular sealing flange means to apply said radial pressing force on said annular sealing flange means; and
   d) connection means for removably connecting said cap means to said barrel means such that said cap means sealingly closes off said first opening.

21. The applicator according to claim 20, wherein said barrel means includes a large diameter cylindrical section, a small diameter cylindrical section and an annular sloped transition section that connects said large diameter cylindrical section and said small diameter cylindrical section, said large diameter cylindrical section, said small diameter cylindrical sect, ion and said annular sloped transition section being formed coaxially with each other, and said plunger means is slidably positioned in said large diameter cylindrical section of said barrel means in sealing contact with the inner surface thereat.

22. The applicator according to claim 21, wherein said plunger means includes a frusto-conical section connected with said cylindrical section of said plunger means, and said annular sealing flange means includes a plurality of annular bead means for providing a seal between said plunger means and the inner surface of the large diameter cylindrical section of said barrel means, while permitting sliding movement of said plunger means in said large diameter cylindrical section of the barrel means.

23. The applicator according to claim 21, wherein said large diameter cylindrical section includes a portion of said inner surface and said second opposite end; and further including retention bead means for engaging with said annular sealing flange means to retain said plunger means in said large diameter cylindrical section, said retention bead means being formed on said portion of the inner surface of said large diameter cylindrical section in spaced relation from the second opposite end thereof.

24. An applicator for introducing a semisolid medicinal into a body cavity comprising:
   a) barrel means for containing the medicinal, said barrel means including:
      i) an inner surface defining an internal cavity for containing the medicinal,
      ii) a first end with a first opening in communication with said internal cavity, and
      iii) a second opposite end with a second opening in communication with said internal cavity,
   b) plunger means for pushing said medicinal through said first opening, said plunger means being slidably positioned in said barrel means in sealing contact with the inner surface thereof, said plunger means including:
      i) a cylindrical section,
      ii) annular sealing flange means for sealing said plunger means against the inner surface of said barrel means, and
      iii) rib means for securing said annular sealing flange means in surrounding and spaced relation to said cylindrical section and for substantially preventing inward radial deformation of said annular sealing flange means when said medicinal is expelled from said barrel means;
   c) removable cap means for sealingly closing off said first opening and for applying an axial pushing force to said plunger means when said cap means is removed from said sealing relationship with said barrel means in order to slidably move said plunger means in said barrel means to expel said medicinal from said first opening; and d) connection means for removably connecting said cap means to said barrel means such that said cap means sealingly closes off said first opening.

25. The applicator according to claim 24, wherein said barrel means includes a large diameter cylindrical section, a small diameter cylindrical section and an annular sloped transition section that connects said large diameter cylindrical section and said small diameter cylindrical section, said large diameter cylindrical section, said small diameter cylindrical section and said annular sloped transition section being formed coaxially with each other, and said plunger means is slidably positioned in said large diameter cylindrical section of said barrel means in sealing contact with the inner surface thereat.

26. The applicator according to claim 25, wherein said plunger means includes a frusto-conical section connected with said cylindrical section of said plunger means, and said annular sealing flange means includes a plurality of annular bead means for providing a seal between said plunger means and the inner surface of the large diameter cylindrical section of said barrel means, while permitting sliding movement of said plunger means in the large diameter cylindrical section of said barrel means.

27. The applicator according to claim 25, wherein said large diameter cylindrical section includes a portion of said inner surface and said second opposite end; and further including retention bead means for engaging with said annular sealing flange means to retain said plunger means in said large diameter cylindrical section, said retention bead means being formed on said portion of the inner surface of said large diameter cylindrical section in spaced relation from the second opposite end thereof.

28. The applicator according to claim 24, wherein said rib means includes a plurality of equiangularly spaced and radially directed ribs connected between said cylindrical section and said annular sealing flange means.

* * * * *